United States Patent
Mustonen et al.

(10) Patent No.: US 6,564,657 B1
(45) Date of Patent: May 20, 2003

(54) SAMPLING METHOD AND APPARATUS FOR CONSISTENCY MEASUREMENT

(76) Inventors: Markku Mustonen, 3730 Willow Mill Dr., Lawrenceville, GA (US) 30244; Ted Quincy Cobb, Jr., 258 Grand Manor Dr., Marietta, GA (US) 30067

( * ) Notice: Subject to any disclaimer, the term of this patent is extended or adjusted under 35 U.S.C. 154(b) by 0 days.

(21) Appl. No.: 08/657,979

(22) Filed: May 30, 1996

(51) Int. Cl.[7] .................................................. G01N 1/14
(52) U.S. Cl. ............................. 73/863.84; 73/863.83; 73/863.23
(58) Field of Search ......................... 73/863.84, 863.85, 73/863.83, 863.81, 863.02, 863.23, 863.24, 863.25, 53.04, 61.72, 64.56, 863.53, 863.54, 863.44

(56) References Cited

U.S. PATENT DOCUMENTS

| | | | | |
|---|---|---|---|---|
| 2,598,535 A | * | 5/1952 | Green | 73/863.83 |
| 3,538,749 A | * | 11/1970 | Danforth | 73/53.04 |
| 3,659,461 A | * | 5/1972 | Thompson | 73/863.54 |
| 4,009,617 A | * | 3/1977 | Johnson | 73/863.84 |
| 4,020,676 A | * | 5/1977 | Nuxhall et al. | 73/61.72 |
| 4,262,533 A | * | 4/1981 | Jaeger | 73/863.83 |
| 4,433,587 A | * | 2/1984 | Risdal | 73/863.54 |
| 4,475,410 A | * | 10/1984 | Jaeger | 73/863.84 |
| 4,635,470 A | * | 1/1987 | Skállen et al. | 73/863.83 |
| 4,890,484 A | * | 1/1990 | Telfer et al. | 73/61.72 |

* cited by examiner

Primary Examiner—Helen Kwok
Assistant Examiner—Nashmiya Fayyaz

(57) ABSTRACT

A sampling device provides accurately repeatable samples for determination of consistency. A chamber is placed into the process line, and a piston in the chamber can be moved rearwardly to withdraw a quantity of process into the chamber. A sample container in communication with the chamber is also filled. The piston is moved forwardly to urge the process back into the process line, while the sample container remains full of process. The sample container has a known volume, and the piston in its forward position closes the sample container so the sample therein is limited to the known volume. The sample is transferred to a filter, and clean water assures that all solids are transferred to the filter.

11 Claims, 2 Drawing Sheets

SAMPLING METHOD AND APPARATUS FOR CONSISTENCY MEASUREMENT

BACKGROUND OF THE INVENTION

1. Field of the Invention

This invention relates generally to consistency measurement for the pulp and paper industry, and is more particularly concerned with a sampling apparatus for accurate, repeatable sampling for the determination of consistency.

2. Discussion of the Prior Art

In the pulp and paper industry it is very important to know the consistency of the process. It is conventional to utilize a consistency transmitter which constantly monitors the consistency and constantly gives a reading. The more highly regarded consistency measurement however is determined by taking a sample by hand, and analyzing the sample. A plurality of samples is generally taken, and an average is used as the actual consistency. Consistency transmitters, the, are calibrated on the basis of the hand sample.

In taking a hand sample, one uses a valve in the process line that can be opened so a beaker can be filled. In a effort to obtain a homogeneous and representative sample, one usually allows the liquid to run from the valve for a period of time before filling the beaker. Also, the nipple to which the valve is fixed extends into the process line, beyond the wall of the line, in an effort to avoid the unrepresentative material at the wall of the process line. Even with these various precautions, it will be understood that a major problem is in simply filling the beaker. No two people will read the markings on the beaker precisely the same, and one person will not be very consistent between a plurality of different samples. Overall, it is thought that the hand sampling for the determination of consistency has errors of about ten percent. It is important to remember that the hand sampling is the standard, and the consistency transmitters are calibrated based on the findings through hand sampling. Thus, there is no highly accurate means for determination of consistencies.

SUMMARY OF THE INVENTION

The present invention provides a sampling method and apparatus that extracts a quantity of material from the process line, and fills a container having a predetermined volume. A larger quantity than required is drawn to be sure a representative sample is taken, and the container is filled from this quantity. The container is then isolated from the process line, and the sample is deposited into a collector. Clean water is used to wash the sample from the container so the container will be ready to receive another sample.

In the preferred embodiment of the present invention the apparatus includes a chamber in communication with the process line, and a piston reciprocable within the chamber. Rearward movement of the piston causes intake of a quantity of the process; and, the piston uncovers the sample container so process runs into the container. The reverse stroke of the piston urges excess process out of the chamber back into the process line, and closes the container so the container has a discrete volume of process therein. When the process is drained from the sample container it is directed to a filter where the fibers are filtered from the liquid component. Thus, the sample taken is accurate, and repeatable to a high degree of accuracy.

BRIEF DESCRIPTION OF THE DRAWINGS

These and other features and advantages of the present invention will become apparent from consideration of the following specification when taken in conjunction with the accompanying drawings in which.

DETAILED DESCRIPTION OF THE EMBODIMENT

Figure 1:
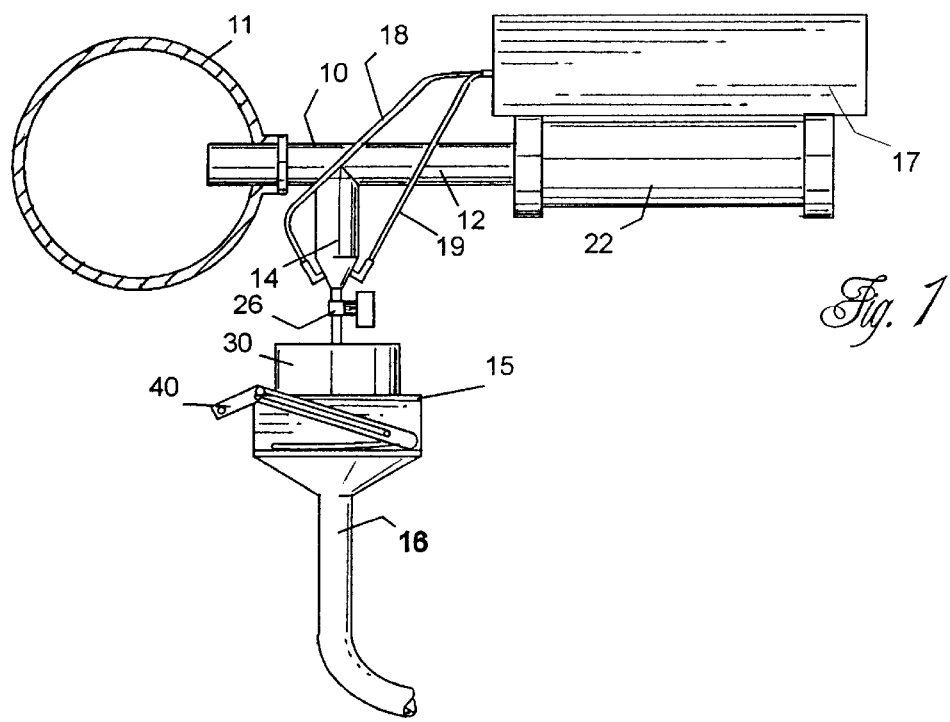
FIG. 1 is a side elevational view of sampling apparatus made in accordance with the present invention, the device being shown in conjunction with a process line.

Referring now more particularly to the drawings, and to that embodiment of the invention here presented by way of illustration, FIG. 1 shows a sampling apparatus generally designated at 10, the apparatus being mounted in communication with a process line 11. The sampling apparatus 10 includes a chamber 12 having a sample container 14 extending therefrom and selectively in communication therewith. A filtering means 15 is disposed to receive the sample from the sample container 14. A piece of filter paper or the like will retain the fibers, while the liquid is allowed to drain through the drain pipe 16.

Continuing to look at FIG. 1 of the drawings, it will be understood that the chamber 12 draws in a quantity of the process from the process line 11 and fills the sample container 14. The sample container 14 is the closed, isolating it from the process line; then, the sample in the sample container is drained into the filtering means 15. To assure that all the solid material is removed from the sample container 14, clean water is introduced through the lines 18 and 19. The inflow of clean water is controlled through an electronic controller 17 which will open valves at appropriate times, and close them at proper times. The electronic signals may be manually controlled, or may be automatic. Those skilled in the art will easily determine the best mode of operation for the particular system.

Figure 2:
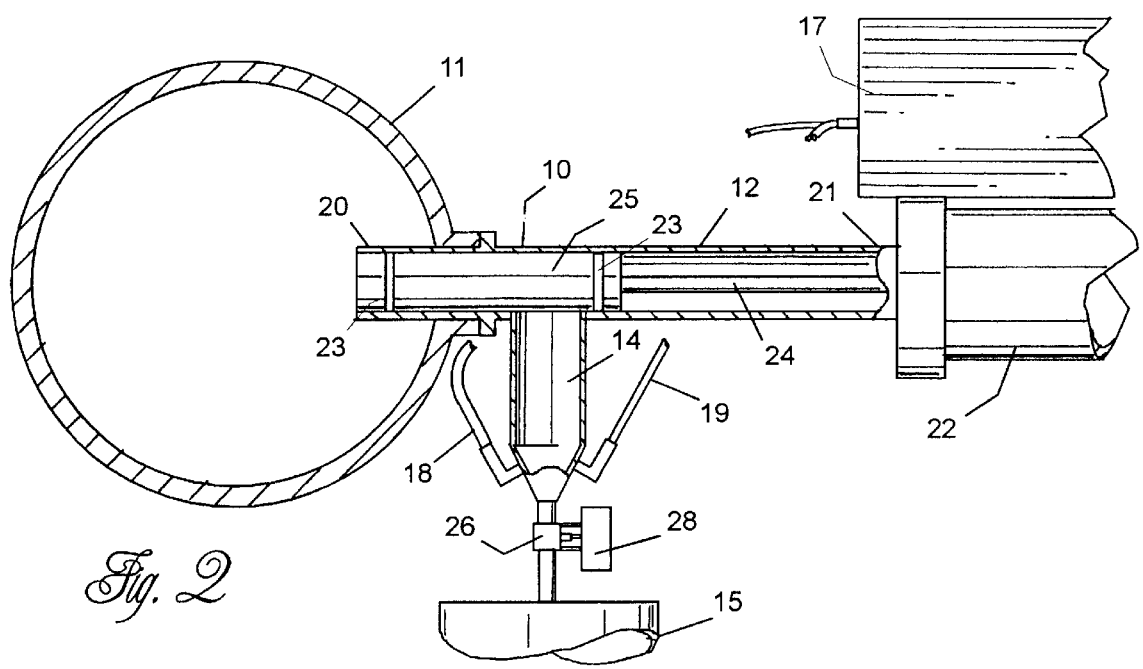
FIG. 2 is an enlarged cross-sectional view of the sampling device shown in FIG. 1, partially broken away.

Attention is now directed to FIG. 2 of the drawings for a more detailed understanding of the construction and operation of the sampling device 10. In FIG. 2 it can be seen that the chamber 12 has one end 20 within the process line 11, and the other end 21 fixed to a fluid operated cylinder 22. The fluid operated cylinder 22 includes a piston rod 24 which is fixed to a piston 25 within the chamber 12. As shown in FIG. 2, the piston rod 24 is fully projected from the fluid operated cylinder 22, and the piston 25 extends substantially to the end 20 of the chamber 12. Thus, the piston 25 completely closes off the sampling device 10 from the process line 11, the piston 25 being sealed with respect to the chamber wall by seals 23.

When fluid enters the fluid operated cylinder 22 to cause the piston rod 24 to be retracted, the piston 25 will move to the right as shown in FIG. 2. In so doing, process can enter the chamber 12. In its furthest retracted position the piston 25 will be disposed to the right of the sample container 14, so the entire area of the chamber 12 and container 14 will fill with process. Once the system is filled, fluid will be redirected in the fluid operated cylinder 22 so the piston rod 24 will be again projected. The piston 25 will move to the left, urging much of the process back into the process line 11, but isolating the sample container 14 with a quantity of process therein.

With each cycle as described above, it will be understood that the sample container 14 will be precisely filled with process. Since the container 14 has a known volume, there will be a sample of a precisely known size; and, the sample is repeatable any number of times with great precision.

Those skilled in the art will understand that, in computing consistency, one weighs the total sample, and weighs the fibers filtered from that sample. Since the volume of the sample is known accurately, the weight of the sample can be known accurately. As a result, the additional water used to wash fibers from the sample container will not distort the calculations. The fibers are collected, dried and weighed so the water makes no difference, but it is important to collect all the fibers from the sample.

Once the sample container 14 has been filled as described above, and isolated as illustrated in FIG. 2, the valve 26 will be opened to allow the sample to drain into the filtering means 15. Any form of valve may be used, but as here shown there is an electrical operating means indicated at 28. An appropriate electrical signal will open the valve 26; and, when the sample has been collected, a different signal will close the valve 26 so the next sample can be collected.

Figure 3:
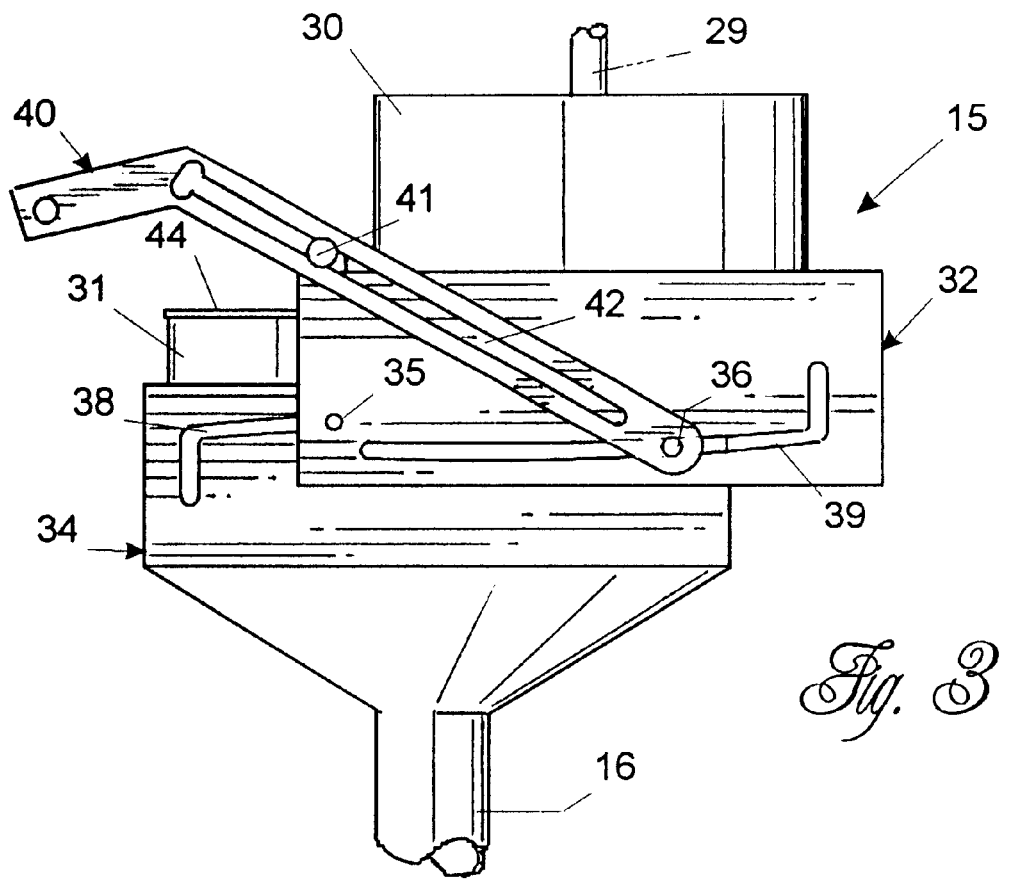
FIG. 3 is an enlarged side elevational view of the filter housing shown in FIG. 1, the housing being partially opened; and, FIG. 4 is a perspective view, partially broken away, showing a filter basket for use with the present invention.
Figure 4:
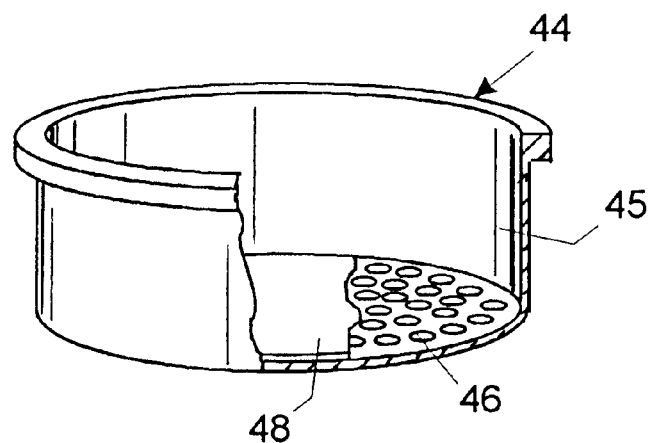

The filtering means 15 is shown in more detail in FIGS. 3 and 4. Here it can be seen that the pipe 29 leading from the valve 26 is connected to an upper canopy 30 of the filtering means 15. The canopy 30 is here indicated as circular, and a filter holder 31 is disposed below the canopy 30.

The filter holder 31 is shown somewhat in FIG. 3, and it will be understood that the filter housing is partially open as shown in FIG. 3 so the filter holder 31 is moved somewhat to one side. When the filtering means 15 is in use the filter housing is closed, as shown in FIG. 1, and the filter holder 31 is disposed directly beneath the canopy 30.

The filter housing includes an upper portion 32 and a lower portion 34. The upper and lower portions are connected by screws, such as the screws 35 and 36, riding in slots 38 and 39. Thus, the screws and slots act as cams and cam followers to determine the path of motion of the lower portion 34 with respect to the upper portion 32.

In more detail, the screw 35 is fixed to the upper portion 32 and is slidable in the slot 38 in the lower portion 34. The screw 36 is fixed to the lower portion 34 and to the arm 40, and is slidable in the slot 39 in the upper portion 32. A guide screw 41 is fixed with respect to the upper portion 32 and is slidable in the slot 42 in the arm 40. Thus, as the arm 40 is pulled forward, or to the left as shown in FIG. 3, the screw 36 will pull the lower portion 34 forward. Opposite motion will realign the lower portion with the upper portion 32.

The filter holder 31 is preferably fixed with respect to the lower portion 34 of the filter housing so the filter will always be properly placed with respect to the canopy 30. For convenience, therefore, there is a removable filter basket 44 shown in more detail in FIG. 4. The filter basket 44 is generally conventional, including a side wall 45 and a perforate bottom 46. While the bottom 46 is here shown as formed integrally with the basket 44, those skilled in the art will recognize that a separate piece of screen wire or other perforate material may be used as the bottom. The important feature is that the bottom 46 supports a filtering medium such as the sheet of filter paper 48, and allows liquid to pass through the filter basket 44.

It will therefore be understood by those skilled in the art that the present invention provides means for extracting a sample from the process line, and the sample size is repeatable with great accuracy. One can use a sample size equal to the volume of the sample container 14, or one can extract multiple sample containers full to make up one sample. In either event, the final sample size is repeatable with great accuracy. If multiple containers full make up one sample, one would empty all containers into the filtering means 15, washing down all fibers with clean water from the lines 18 and 19, so all fibers will be collected on a single piece of filter paper.

The dried fibers will be weighed to determine the weight of fibers in the sample. Knowing the precise volume of the sample, the total weight of the sample can be easily determined. With these two factors, the consistency is easily computed.

It will therefore be understood by those skilled in the art that the particular embodiment of the invention here presented is by way of illustration only, and is meant to be in no way restrictive; therefore, numerous changes and modifications may be made, and the full use of equivalents resorted to, without departing from the spirit or scope of the invention as outlined in the appended claims.

What is claimed is:

1. Sampling apparatus, for use in taking a sample of process from a process line, said sampling apparatus comprising a chamber extending into said process line and in communication with said process line, piston means reciprocable within said chamber, a sample container contiguous with and in communication with said chamber, said sample container having a fixed volume, said piston means having a first position within said chamber and in said process line whereby said piston means blocks communication with said sample container and isolates said sample container from said process line, and a second position wherein said piston means is retracted to allow communication between said process line and said sample container through said chamber.

2. Sampling apparatus as claimed in claim 1, wherein said piston means, in said first position, closes said sample container so that said sample container comprises said fixed volume.

3. Sampling apparatus as claimed in claim 2, and further including water lines connected to said sample container for washing said sample from said sample container.

4. Sampling apparatus as claimed in claim 1, and further including means for selectively moving said piston from said first position to said second position and from said second position to said first position.

5. Sampling apparatus as claimed in claim 1, said chamber including a first end within said process line and a second end externally of said process line, said piston in said first position being substantially at said first end of said chamber for excluding process from said chamber.

6. Sampling apparatus as claimed in claim 1, and including filtering means for receiving a sample from said sample container.

7. Sampling apparatus as claimed in claim 6, and including valve means between said sample container and said filter means, said filter means comprising a drain for disposing of liquid, and a filter for retaining solids from said sample.

8. A method for sampling process for making consistency measurements, said method comprising the steps of inserting a chamber into the process line, said chamber having a sample container of known volume contiguous thereto and in communication therewith, moving a piston rearwardly in said chamber for providing communication between said process line and said sample container through said chamber for allowing said process to fill said sample container, moving said piston forwardly to close said sample container while retaining the process sample within said sample container.

9. A method as claimed in claim 8, and including the step of subsequently draining said sample container into a filtering means, and thereby collecting the solids in said process sample while allowing liquid to drain from the sample.

10. A method as claimed in claim 9, and further including the step of admitting clean water into said sample container for washing said process sample from said sample container, and collecting any solids with said filtering means.

11. A method as claimed in claim 10, wherein said steps of moving a piston rearwardly in said chamber and moving said piston forwardly in said chamber are repeated so that said filtering means collects solids from a plurality of process samples.

\* \* \* \* \*